United States Patent [19]

Grossman

[11] Patent Number: 5,711,943
[45] Date of Patent: Jan. 27, 1998

[54] TOPICAL HAIR THICKENER OF GELATIN, FILM-FORMING POLYMER AND THICKENER

[76] Inventor: Leslie Grossman, 3449 S. Uravan Way, Unit 2, Apt. 303, Aurora, Colo. 80013

[21] Appl. No.: 799,106

[22] Filed: Feb. 11, 1997

Related U.S. Application Data

[63] Continuation-in-part of Ser. No. 457,610, Jun. 1, 1995, Pat. No. 5,601,812.

[51] Int. Cl.$^6$ ............................................. A61K 07/06
[52] U.S. Cl. ............................ 424/70.15; 424/70.11; 424/70.16
[58] Field of Search ................. 424/70.15, 70.11, 424/70.16; 514/2; 524/22

[56] References Cited

U.S. PATENT DOCUMENTS

| | | | |
|---|---|---|---|
| 2,704,269 | 3/1955 | Tice | 167/82 |
| 3,840,338 | 10/1974 | Zviak et al. | 424/70.9 |
| 3,954,725 | 5/1976 | Johnsen et al. | 424/70.17 |
| 3,958,581 | 5/1976 | Abegg et al. | 424/70.16 |
| 4,208,402 | 6/1980 | Bore et al. | 424/70.14 |
| 4,749,684 | 6/1988 | Silvestrini | 514/202 |
| 4,940,578 | 7/1990 | Yoshihara et al. | 424/70.16 |

OTHER PUBLICATIONS

Lindo et al., Human Hair Symposium, [Pap.], 1st, Meeting Date 1973, pp. 135–144, Editors: Brown, Algie C. Publisher: MEDCOM Press, New york, N.Y. 1974.

Scala et al., "Effect of Daily Gelatin Ingestion on Human Scalp Hair", Nutrition Reports International, vol. 13, No. 6, pp. 579–592 Jun. 1976.

*Primary Examiner*—Robert E. Sellers
*Attorney, Agent, or Firm*—Lerner, David, Littenberg, Krumholz & Mentlik

[57] ABSTRACT

Hair thickening compositions for topical applications containing an aqueous gelatin solution having a concentration between about 0.30 and about 15% by weight and further including a water-soluble cosmetic film-forming polymer at a concentration greater than 60% of that of the gelatin and between about 0.10 and about 15% by weight, a thickening agent, and an acid neutralizing agent in an amount effective to maintain the solution at a pH range between about 6.0 and 9.5, within which the gelatin and film-forming polymer are stable together in aqueous solution at their respective concentrations. Methods for preparing stable aqueous solutions containing gelatin and a water-soluble film-forming polymer are also disclosed, as well as methods for increasing hair shaft thickness by topical application of the inventive hair thickening compositions to the hair.

9 Claims, No Drawings

TOPICAL HAIR THICKENER OF GELATIN, FILM-FORMING POLYMER AND THICKENER

CROSS-REFERENCE TO RELATED APPLICATIONS

This application is a continuation-in-part of U.S. Pat. application Ser. No. 08/457,610 filed Jun. 1, 1995, which issued as U.S. Pat. No. 5,601,812 on Feb. 11, 1997.

BACKGROUND OF THE INVENTION

The present invention relates to hair thickening and conditioning compositions, and in particular to aqueous gelatin solutions, the application of which to the hair results in a significant increase in hair shaft thickness. The present invention also relates to methods for preparing the gelatin compositions of the present invention, as well as to methods for increasing hair shaft thickness by topical application to the hair of the gelatin compositions of the present invention.

U.S. Pat. No. 4,749,684 discloses that the ingestion of gelatin promotes an increase in the linear growth rate of hair. Scala et al., *Nutr. Rep. Int.*, 13(6), 579–92 (1976) discloses that dietary supplementation with gelatin produces an increase in hair thickness. The ability to increase hair thickness by the topical application of gelatin is unreported.

Hair coated with gelatin is difficult to comb in the absence of a conditioning agent, but stable solutions of gelatin with a conditioning agent have been heretofore unknown. Lindo et at., "Hair Processing and Conditioning," *Hum. Hair Sym.* [*Pap.*], 1st, (Brown, Editor, MEDCOM Press, New York 1974 (Meeting Date 1973)) pages 135–44 reports the capability of hair to absorb topically applied hydrolyzed gelatin, but with little substantivity, so that little gelatin remains after thorough washing with room temperature water.

U.S. Pat. No. 4,208,402 discloses a topical solution for improving the appearance of oily hair or skin, including the scalp, containing from about 0.5 to 1.5% by weight of gelatin and from 0.15 to 0.45% by weight of partially hydrolyzed polyvinyl acetate in aqueous or hydroalcoholic solution. The level of film-forming polymer disclosed is insufficient to provide a readily combable product. By the manufacturing process disclosed, aqueous solutions cannot be formed with higher concentrations of the film-forming polymer without the gelatin precipitating from the solution.

Topical application of gelatin to hair would be possible if stable aqueous solutions containing higher concentrations of film-forming polymers could be prepared. The inability to comb hair to which gelatin solutions have been topically applied has prevented the recognition that topical gelatin application increases hair shaft thickness.

There remains a need for stable aqueous gelatin solutions containing higher levels of film-forming polymer to provide gelatin solutions for topical hair application that do not resist combing.

SUMMARY OF THE INVENTION

This need is met by the present invention. It has now been discovered that stable aqueous gelatin solutions can be prepared with levels of film-forming polymer greater than or equal to that of the gelatin by carefully maintaining an essentially neutral solution pH, while dissolving the gelatin and the film-forming polymer together. It has further been discovered that the topical application of such gelatin solutions to the hair leaves the hair easy to comb and produces a significant increase in hair shaft thickness, as confirmed by independent laboratory testing.

Therefore, in accordance with the present invention, a hair thickening composition for topical application is disclosed in the form of an aqueous gelatin solution having a concentration between about 0.30 and about 15% by weight and further including a water-soluble cosmetic film-forming polymer at a concentration greater than 30% that of the gelatin and between about 0.10 and about 15% by weight, wherein the solution is within a pH range at which the gelatin and the film-forming polymer are stable together in aqueous solution at their respective concentrations.

The present invention also provides a method for preparing stable aqueous solutions containing gelatin and a water-soluble cosmetic film-forming polymer. In accordance with this aspect of the present invention, a method for preparing a stable aqueous solution of gelatin and a water-soluble cosmetic film-forming polymer is disclosed, which method includes the steps of:

dissolving up to about 30% by weight of gelatin in a first quantity of water, so that an aqueous gelatin solution concentrate is formed;

dissolving up to about 30% by weight of a water-soluble cosmetic film-forming polymer in a second quantity of water, while maintaining the solution pH between about 6.0 and about 9.5 as the polymer is added to the second quantity of water, so that an aqueous polymer solution is formed; and mixing the aqueous gelatin solution concentrate with the polymer solution while maintaining the solution pH between about 6.0 and about 9.5, so that a stable aqueous solution of gelatin and polymer is formed.

By carefully maintaining the solution pH between about 6.0 and about 9.5, it is possible to form solutions containing elevated concentrations of gelatin and water-soluble cosmetic film-forming polymers. Such polymer concentrations provide a product that conditions and detangles the hair, while at the same time providing a significant increase in hair shaft thickness. As an added benefit, applied product may have its holding ability reactivated by simply applying a fine mist of water to re-moisten the hair, giving it the ability to be re-set by combing or brushing into place again.

As will be readily appreciated, the method of the present invention may be utilized to prepare a product concentrate that may be diluted with a solvent selected from water and cosmetically acceptable alcohols to obtain the hair thickening compositions of the present invention. Methods in accordance with the present invention may therefore further include the step of diluting the stable aqueous solution of gelatin and polymer with a solvent selected from water and cosmetically acceptable alcohols so that an aqueous solution containing between about 0.30 and about 15% by weight of gelatin and a water-soluble cosmetic film-forming polymer at a concentration greater than 30% that of the gelatin and between about 0.10 and about 15% by weight.

Thus, it will be appreciated that concentrates capable of being diluted to form the hair thickening compositions of the present invention are also included within the scope of the present invention. Concentrates in accordance with the present invention have a viscosity between about 4,000 and about 400,000 cps. at room temperature and a polymer to gelatin ratio between about 6:10 and about 50:1.

The foregoing method makes possible for the first time the preparation of aqueous solutions containing water-soluble film-forming polymer concentrations greater than 30% of the gelatin concentration. This, in turn, led to the discovery of the beneficial hair shaft thickening effects resulting from the topical application of gelatin to the hair. Therefore, in accordance with another aspect of the present invention, a method for increasing hair shaft thickness is disclosed, which method topically applies in an amount sufficient to impregnate the hair an aqueous solution of gelatin at a solution concentration between about 0.30 and about 15% by weight and a water-soluble cosmetic film-forming polymer at a solution concentration greater than 30% that of the gelatin and between about 0.10 and about 15% by weight, wherein the solution is within a pH range at which the gelatin and the film-forming polymer are stable together at their respective concentrations.

The solution preparation method of the present invention may be utilized to prepare hair thickening compositions in a variety of forms suitable for topical application to the hair. The hair thickening compositions of the present invention may be in the form of gels, lotions, creams, mousses, tonics, hair dyes, coloring agents and aerosol or pump-dispensed hair setting sprays and hair conditioning products. The compositions of the present invention are particularly versatile because, in addition to thickening the hair shaft, the compositions provide a hardening, or "setting," effect upon application that softens with combing without diminishing the hair shaft thickening effect. Thus, individuals seeking a hair "setting" effect would simply apply the composition and set the hair, while individuals preferring a softer, natural feel, would simply comb or brush the hair after the product is applied and set. Hair can be re-set by simply applying a water mist and allowing the hair to dry.

The gelatin solutions of the present invention, by containing elevated levels of film-forming polymer, and the inventive methods by which such solutions are prepared, possess novelty independent of the hair thickening effect provided by the topical application of the solutions to the hair. Thus, the compositions of the present invention, and the methods by which they are prepared, may be used to prepare essentially any aqueous composition for topical application to the skin, hair or scalp containing elevated levels of gelatin and film-forming polymer. In fact, the compositions of the present invention and the methods by which they are prepared may be employed with essentially any end-use application that would benefit from the combination of gelatin with a film-forming polymer.

DETAILED DESCRIPTION OF THE PREFERRED EMBODIMENT

The present invention provides aqueous gelatin solutions that significantly increase hair shaft thickness upon topical application to the hair. Unlike prior art gelatin-based hair treatment compositions, the compositions of the present invention contain levels of water-soluble cosmetic film-forming polymers that leave the hair easy to comb following topical application of the product. Until now, it was not possible to prepare gelatin solutions containing levels of film-forming polymers disclosed herein.

Essentially any commercially available gelatin suitable for use in cosmetic products may be used for the hair thickening compositions of the present invention. This would include Type A gelatin derived from pork skin and ranging in molecular weight or viscosity from 50 to 300 bloom, and Type B gelatin prepared from calf skin or bone and ranging in molecular weight or viscosity between 50 and 300 bloom. Type A 250 bloom gelatin is preferred. However, essentially any amino acid solution or colloid equivalent to gelatin may be used in the composition of the present invention.

The hair thickening compositions of the present invention will contain between about 0.30% and about 15% by weight of gelatin, and preferably between about 1 and about 5% by weight of gelatin. A gelatin concentration of 1.3% is most preferred.

Essentially any water-soluble cosmetic film-forming polymer is suitable for use with the hair thickening compositions of the present invention. Representative polymers include polyvinyl pyrrolidone (PVP), polyvinyl acetate, partially hydrolyzed polyvinyl acetate, copolymers of PVP and vinyl acetate, polyvinyl alcohol, acrylate-acrylamide copolymers, acrylate-PVP copolymers, and the like. Suitable polymers have a number-average molecular weight ranging between about 5,000 and 100,00 daltons, and preferably fall within a molecular weight range between about 10,000 and about 50,000 daltons.

The preferred water-soluble cosmetic film-forming polymer is PVP. Cosmetic-grade PVP is available from BASF under the brand designation LUVISCOL. The grade of LUVISCOL having a molecular weight of about 45,000 daltons is most preferred. The equivalent grade of PVP manufactured by ISP of Linden, N.J. is also suitable.

The quantity of polymer to be employed, as will the quantity of gelatin, will vary depending upon the molecular weight and the desired viscosity of the final product. In addition, the level of polymer employed should be that amount sufficient to leave the hair easy to comb following topical application of the composition of the present invention. That amount is greater than 30% of the gelatin concentration, and in fact may exceed the gelatin concentration, and ranges between about 0.10 and about 15% by weight. A polymer concentration between about 2.5 and about 7.5% by weight is preferred, provided that the concentration of polymer is greater than 30% that of the gelatin. A polymer concentration of about 5.6% is most preferred.

To promote the hair thickening effect of the compositions of the present invention, the concentration of polymer is preferably greater than 60% that of the gelatin, and even more preferably is greater than 90% that of the gelatin. Most preferably, the amount of polymer exceeds that of the gelatin.

Suitable hair thickening compositions in accordance with the present invention will range in viscosity between about 500 and about 80,000 cps. measured at 25° C. Viscosities between about 2,000 and 55,000 cps. are preferred, while a viscosity ranging between about 35,000 and 45,000 cps. is most preferred.

Depending upon the choice of gelatin and polymer molecular weight, it may be necessary to add a thickening agent to the composition of the present invention in order to obtain the desired viscosity. Preferred thickening agents include polymeric materials, such as the CARBOPOL series of polyacrylic acid and cross-linked polyacrylic acid thickening agents and the ULTREX series of poly(diphenyl sulfone) thickening agents, both of which are available from B. F. Goodrich. CARBOPOL 941 and ULTREX 10 are particularly preferred. Other suitable thickening agents include modified starches, vegetable gums and other conventional thickening agents suitable for cosmetic use.

Hair thickening compositions in accordance with the present invention typically contain between about 0% and about 5.0% by weight of thickening agent. A thickening agent level between about 0.2% and about 0.5% by weight is preferred, while a thickening agent level of 0.3% by weight is most preferred.

Water-soluble cosmetic film-forming polymers such as PVP lower the pH of aqueous solutions in which they are dissolved, thereby reducing the solubility of gelatin therein. Gelatin likewise reduces the pH of aqueous solutions in which it is dissolved, so that as the amount of gelatin dissolved in an aqueous solution increases, the amount of additional gelatin that can be further dissolved in that solution significantly decreases. This effect is even more pronounced when a pH-lowering film-forming polymer such as PVP is dissolved in solution.

Therefore, in order for aqueous solutions of gelatin and polymers such as PVP to remain stable at the concentrations disclosed by the present invention, the pH of the solutions must be maintained above a pH at which the gelatin and polymer do not precipitate out of solution, typically above about 6.5 for PVP, although this will vary somewhat for other polymers.

For purposes of the present invention, a composition is considered "stable" if it is consistently capable of being stored at about room temperature for at least about two weeks without separation or precipitation of individual components. Indefinite stability is, of course, ideal. The minimum pH at which a given polymer will be compatible with gelatin can be readily determined by one of ordinary skill in the art without undue experimentation.

The solution pH should also be maintained below the pH at which the gelatin and polymer precipitate out of solution. Polymers such as PVP remain stable with gelatin up to a pH of about 8.5. Higher pH's may be employed with a sacrifice of long-term stability. The PVP-based compositions of the present invention possess indefinite stability at a pH between about 6.9 and about 7.5.

To maintain the pH within this range, an acid neutralizing agent is added to the film-forming polymer-containing gelatin solutions of the present invention while the solutions are being prepared, typically, by first dissolving the film-forming polymer with the addition of an acid neutralizing agent to maintain the pH within the required range while the polymer is being dissolved. A gelatin concentrate is then added to the polymer solution with further addition of the acid neutralizing agent to maintain the pH within the required range.

Essentially any acid neutralizing agent suitable for use with cosmetic products may be used. Examples of suitable acid neutralizing agents include triethanol amine (TEA), which is preferably added in the form of a 99% solution, sodium hydroxide, and the like. TEA is most preferred.

The amount of acid neutralizing agent added to the hair thickening compositions of the present invention will depend upon the amount of pH drop caused by the gelatin and film-forming polymer, which will in turn depend upon the amount of each ingredient used and the lot to lot variation in acidity. However, compositions in accordance with the present invention will typically contain less than 2% by weight of TEA, and will more typically contain about 0.5% by weight of TEA.

The hair thickening compositions of the present invention may optionally include up to about 5% by weight of a preservative that functions as an anti-bacterial agent and/or an antioxidant. Methylparaben is a preferred antioxidant because it functions as both an anti-bacterial agent and an antioxidant. The compositions of the present invention may also be perfumed and/or colored for purposes of appearance, if desired. In addition, the compositions may optionally include conventional levels of a hair dye or hair coloring agent. Conventional levels of well-known UV-absorbing sunscreening agents may also be used. Hair conditioning agents in addition to the soluble film-forming polymer such as N-pantoyl-3-propanolamine (Panthenol) may also be included. Conventional hair product additives such as vitamin E, jojoba oil, aloe extract, herbal extracts, and the like may also be included.

The remainder of the compositions of the present invention consists essentially of solvent, at levels that can exceed 99% by weight. In most instances, the solvent will consist entirely of water. However, lower viscosity products such as hair setting compositions for aerosol or pump spray application may use an alcohol-water solvent combination. Therefore, compositions in accordance with the present invention may optionally contain up to about 90% by weight of a cosmetically acceptable alcohol, such as ethanol, isopropanol, and the like.

The hair thickening compositions of the present invention may also be prepared in the form of gels, creams, mousses, hair tonics, lotions, aerosols, pump sprays, dyes, hair conditioning products and coloring agents using conventional cosmetic product formulation techniques. This would include the preparation of oil-in-water or water-in-oil emulsions and microemulsions based upon the aqueous gelatin solutions of the present invention. The preparation of such emulsions and microemulsions is essentially conventional and involves the combination of the aqueous solutions of the present invention with an oil phase and a suitable emulsifier.

The hair thickening compositions of the present invention are prepared by first making a concentrated aqueous gelatin solution. The aqueous gelatin solution concentrate should contain up to about 30% by weight of gelatin that is prepared by combining the gelatin with water at a temperature between about 100° F. and about 170° F. and preferably about 140° F. The two ingredients are combined with mixing until the gelatin is completely dissolved. At this stage, pH is not critical and therefore, the gelatin pH is not adjusted.

A separate solution of the water-soluble cosmetic film-forming polymer is prepared. Polymer and water are also combined with heating at a temperature between about 80° F. and about 150° F., and preferably at about 120° F. Here, pH is important, but a broader range may be employed because long-term product stability is not a factor at this stage. Any thickening agent, preservative or other optional ingredient should be dissolved in the water before the film-forming polymer is added. The film-forming polymer is added in increments, typically about 20 pounds. Each incremental quantity is mixed until completely dissolved, after which the pH is checked, and acid neutralizing agent is added, if needed, in an amount sufficient to maintain the solution pH between about 5.0 and about 9.5, and preferably, at this stage, between about 5.0 and about 7.0 in order to maintain an easier to mix viscosity. The incremental addition of polymer followed by pH measurement and adjustment is repeated until the amount of polymer to be added is completely dissolved and the polymer solution is at a pH within the 5.0 to 9.5 range, and again, preferably between 5.0 and 7.0.

The gelatin concentrate is then added to the polymer solution, again in incremental quantities, typically 50 pounds at a time, so as not to shock the solution pH and precipitate the gelatin. Following each incremental addition, the solution is stirred to dissolve the gelatin concentrate in the aqueous polymer solution, after which pH is measured and adjusted following the procedure utilized for the preparation of the polymer solution. Incremental addition of gelatin concentrate followed by pH measurement and adjustment is repeated until the gelatin concentrate is completely dissolved in the polymer solution within a pH range of 5.0 to 9.5 and preferably between 5.0 and 6.0.

Any remaining ingredients are then added. A final quantity of acid neutralizing agent is added, if necessary, to bring the product within a 6.5 to 8.5 pH range and now preferably between 6.9 and 7.5. A quantity of water is then added, calculated to bring the final product within the desired batch volume. The product is then cooled and packaged by conventional techniques.

As can be readily appreciated, the compositions of the present invention can be prepared as concentrates suitable for dilution by distributors or the ultimate consumer to obtain the hair thickening compositions of the present invention. Such concentrates are considered to be within the scope of the present invention and may be prepared by omitting all or part of the final water addition step and even some of the water in the gelatin concentrate and polymer solution. Concentrates in accordance with the present invention have a viscosity between about 4,000 and about 400,000 cps. at room temperature and a polymer to gelatin ratio between about 3:10 and about 50:1.

A particularly preferred formulation is set forth below, listing preferred ranges of ingredients and the optimum concentration in weight-percent for each:

| INGREDIENT | RANGE | OPTIMUM |
|---|---|---|
| PVP (45 k $Mw_n$) | 0.1–15% | 5.6% |
| 250 bloom Type A gelatin | 0.3–15% | 1.3% |
| Cross-linked polyacrylic acid thickener | 0–5% | 0.3% |
| Triethanol amine (99% aqueous solution) | 0–2% | 0.5% |
| Methylparaben preservative | 0–5% | 0.25% |
| Perfume | 0–5% | 0.28% |
| Deionized water | q.s. | 92.3% |

The method of the present invention for increasing hair shaft thickness topically applies the hair thickening compositions of the present invention to the hair in an amount sufficient to impregnate the hair. Generally from about 2 to about 20 mL of the hair thickening composition is applied to the hair, although longer hair may require significantly larger quantities.

Consistent results are achieved when the compositions of the present invention are applied to moist towel-dried hair following shampooing. The hair thickening composition may be massaged into the hair, spread evenly with comb or brush, set with rollers or blown dry with styling. Alternatively, it may be lightly sprayed on the surface of the hair, in which case it functions as a "setting" product. Daily, in-between shampooing, the hold may be reactivated without the addition of more product by simply applying a mist of water and re-setting the hair as previously described. The hair thickening and setting compositions of the present invention are removed by washing the hair.

Compositions in accordance with the present invention provide at a minimum at least a 5–10% increase in hair shaft thickness, or diameter, up to about a 25% increase, and greater. The increase in hair shaft thickness has been confirmed by independent laboratory testing, as set forth in the examples below. The thickness increase is attributable to the gelatin component of the composition, the consistent topical application and combability of which would not be possible without the level of water-soluble cosmetic film-forming polymer employed. The present invention provides a means by which aqueous solutions of gelatin can be prepared with elevated levels of film-forming polymer in order to provide a suitable product for topical application to the hair.

The following non-limiting examples set forth hereinbelow illustrate certain aspects of the invention. All parts and percentages are by weight, unless otherwise noted.

EXAMPLES

EXAMPLE 1

PREPARATION OF HAIR THICKENING GEL

A gel solution in accordance with the present invention was prepared by first dissolving 29 pounds of 250 bloom Type A gelatin (Hormel) in 300 pounds of water in a heated mixer equipped with stirring blades. The gelatin and water were mixed with heating to 140° F. until a uniform homogeneous mixture was formed. The resulting mixture was maintained at 140° F.

In a separate steam jacketed mixer with stirring blades, six pounds of CARBOPOL 941 and five pounds of methylparaben (Mallincrodt) preservative were combined with 1,500 pounds of water. The ingredients were mixed with heating to 120° F. until a uniform homogeneous mixture was formed. The pH of a sample of the mixture was checked and determined to be 3.3. 32 oz. TEA was added to bring the pH to 4.5.

112 pounds of LUVISCOL K-30, a PVP having a number-average molecular weight of 45,000 daltons, was added to this mixture in 20 pound increments. Upon addition of the first 20 pounds of the PVP, the ingredients were mixed with heating to 120° F. until the PVP was completely dissolved. The pH of a sample was checked and determined to be 5.45. Because this was at the low end of the desired pH range, 32 oz. of a 99% aqueous solution of TEA (Union Carbide) was added with mixing until uniformly dispersed. The pH of a sample was checked again and determined to be mid-range of the preferred initial 5.0–7.0 pH range providing a lower, easier to mix viscosity. Twenty additional pounds of PVP was added to the mixture and stirred with heating to 120° F. until the PVP was completely dissolved. The procedure of adjusting the pH, adding more PVP and readjusting the pH was repeated until all 112 pounds of PVP was added to the mixture.

The amount of TEA that should be added to the mixture to adjust the pH is readily determined by one of ordinary skill in the art without undue experimentation.

Once all the PVP is dissolved in solution, the previously prepared gelatin concentrate is then added in 50 pound increments, with the pH of the mixture being adjusted within a 5.0 to 6.0 range following each incremental adjustment.

Thus, 50 pounds of the gelatin solution was added to the PVP solution. The ingredients were mixed with heating to 140° F. until uniform homogeneous mixture was formed. The pH of a sample was checked and determined to be 5.28. Another 32 oz. of 99% aqueous TEA was added to the mixture with stirring until uniformly dispersed. The pH of a sample was then checked and determined to be 5.75.

Because the pH was within the range of 5.0 to 6.0, 50 more pounds of the concentrated gelatin solution was added to the PVP-gelatin mixture that was stirred with heating to 140° F. The pH was checked again, and the TEA solution was added to the mixture to bring the pH back within the range of 5.0 to 6.0.

The procedure of adjusting the pH, adding more gelatin concentrate, and readjusting the pH was repeated until all 329 pounds of the gelatin concentrate was added to the mixture.

Water was added to bring the total batch size to 1,995 pounds. The mixture was stirred until uniform and a final pH measurement of a sample was made. The product was then cooled to room temperature with continuous mixing. At room temperature, five pounds of perfume was added and stirred until uniform. A final addition of 4.5 lbs. of TEA was made to bring the product pH to 7.2 and stirred until uniform. The product was then packaged in 180 mL squeeze bottles using automated equipment.

PERFORMANCE EVALUATION

The material of Example 1 and three hair samples were sent to an independent laboratory for evaluation. The laboratory described the hair samples as follows:

Five strands of thin, light gray hair labeled "natural clean hair."

A taped bundle of about 100 strands of light grayish and brownish hairs, and several black hairs.

A taped bundle of about 100 strands of thin, straight, dark black hair.

The laboratory was unaware that the second sample of light grayish and brownish hairs with several black hairs were synthetic, rather than natural hairs.

The ends of three strands of the "natural clean hair" were taped together. The loose strands of hair were washed for one minute using a 1.6% solution of TWEEN® 20 in cold water. After washing, the hairs were rinsed under cold tap water for 30 seconds. After rinsing, the hairs were dried for about 60 seconds using a hot air blower at a distance of 12–15 inches until the strands separated.

Sections of about 50 hairs were cut six to eight inches in length from the strands of hair from the other two samples. One end of each hair section was taped, respectively. The loose strands of hair were washed for one minute using a 1.6% solution of TWEEN® 20 in cold water. After washing, the hairs were rinsed under cold tap water for 30 seconds. After rinsing, the hairs were dried for about 90 seconds using a hot air blower at a distance of 12–15 inches until the strands separated.

After drying, the widths of a number of hairs of all three samples were measured using the ocular scale of a Bausch & Lomb stereoscope at a magnification of 25×. The apparent widths of the hair samples were reported in mils (1 mil= 0.001").

Loose ends of each sample were then wetted for 15 seconds under cold tap water. After wetting, the hair thickening composition of Example 1 was massaged on each wet hair sample for 5–10 seconds, while gently removing the excess gel with light finger pressure. Each treated hair sample was dried using a hot air blower for several minutes. As the treated hair samples dried, they tended to bond together and were stiffer. The bonded hair strands were separated by gently twisting the treated strands of hair apart. After the treatment, the widths of a number of hairs of each treated hair sample were measured using the ocular scale of a Bausch & Lomb stereoscope at a magnification of 25×. The results are set forth in the table below.

| | HAIR SAMPLES | | |
|---|---|---|---|
| | "Natural Clean" | Light Gray/Brown | Black |
| Before Treatment | | | |
| # Of Measurements | 20 | 25 | 25 |
| Average Width | 2.5 | 3.8 | 2.8 |
| Standard Deviation | 0.7 | 0.6 | 0.4 |
| After Treatment | | | |
| # Of Measurements | 18 | 25 | 25 |
| Average Width | 3.1 | 3.8 | 3.4 |
| Standard Deviation | 0.5 | 0.9 | 0.6 |

Unknown to the laboratory, the hair samples that were natural hair measured significantly thicker in width after application of the hair thickening composition of Example 1. The synthetic hair sample did not increase in width after application of the hair thickening composition.

EXAMPLE 2

PREPARATION OF SPRAYABLE HAIR SETTING PRODUCT 8 oz. of SD40 alcohol (40% specially denatured ethanol in water) is added to 8 oz. of the product of Example 1. The final composition was easily sprayed from a conventional pump-spray device. The viscosity was also suitable for aerosol application.

The present invention thus provides a proven means by which an actual and significant increase in hair shaft thickness may be produced. Conveniently, the hair thickening compositions of the present invention can be prepared in the form of conventional hair care products, so that the hair thickening treatment method of the present invention can be adopted by an individual without significant changes in their daily hair care regimen.

The foregoing examples and description of the preferred embodiment should be taken as illustrating, rather than limiting, the present invention as defined by the claims. As will be readily appreciated, numerous variations and combinations of the features set forth above can be utilized without departing from the present invention as set forth in the claims. All such modifications are intended to be included within the scope of the following claims.

What is claimed is:

1. A hair thickening composition for topical application comprising an aqueous solution of gelatin at a concentration between about 0.30 and about 15% by weight and a water-soluble cosmetic film-forming polymer at a concentration greater than 60% that of said gelatin and between about 0.10 and about 15% by weight, a thickening agent, and an acid neutralizing agent in an amount effective to maintain said solution at a pH range between about 6.0 and about 9.5, within which said gelatin and said film-forming polymer are stable together at their respective concentrations.

2. The hair thickening composition of claim 1, wherein said pH is between about 6.5 and about 8.5.

3. The hair thickening composition of claim 2, wherein said pH is between about 6.9 and about 7.5.

4. The hair thickening composition of claim 1, wherein said gelatin is selected from the group consisting of 50 to 300 bloom Type A pork skin gelatin and 50 to 300 bloom Type B calf skin and bone gelatin.

5. The hair thickening composition of claim 1, wherein said cosmetic film-forming polymer is selected from the group consisting of polyvinyl acetate, hydrolyzed polyvinyl acetate, vinyl pyrrolidone, copolymers of vinyl acetate and vinyl pyrrolidone, polyvinyl alcohol, acrylate-acrylamide copolymers, and acrylate-polyvinyl pyrrolidone copolymers.

6. The hair thickening composition of claim 1, wherein said thickening agent is a crosslinked polyacrylic acid.

7. The hair thickening composition of claim 1, wherein said aqueous solution comprises up to about 90% by weight of ethanol or isopropanol.

8. The thickening composition of claim 1, wherein said acid neutralizing agent is triethanol amine.

9. The hair thickening composition of claim 1, wherein said polymer concentration exceeds that of said gelatin.

* * * * *

UNITED STATES PATENT AND TRADEMARK OFFICE
CERTIFICATE OF CORRECTION

| | | |
|---|---|---|
| PATENT NO. | : | 5,711,943 |
| DATED | : | January 27, 1998 |
| INVENTOR(S) | : | Grossman |

It is certified that error appears in the above-identified patent and that said Letters Patent is hereby corrected as shown below:

Column 5, line 63, "to the soluble film-forming"
should read --to the water-soluble film-forming--.

Column 9, line 9, ""natural dean hair"
should read --natural clean hair--.

Signed and Sealed this

Twelfth Day of May, 1998

*Attest:*

BRUCE LEHMAN

*Attesting Officer*  *Commissioner of Patents and Trademarks*